United States Patent
Schwenn et al.

(10) Patent No.: US 6,589,195 B1
(45) Date of Patent: Jul. 8, 2003

(54) MODULAR ADJUSTABLE PROPHYLACTIC HIP ORTHOSIS AND ADDUCTION/ABDUCTION JOINT

(75) Inventors: Shannon R. Schwenn, Deltona, FL (US); Alan T. Sandifer, Winter Springs, FL (US); Kenneth P. Davis, High Wycombe (GB)

(73) Assignee: Orthomerica Products, Inc., Newport Beach, CA (US)

( * ) Notice: Subject to any disclaimer, the term of this patent is extended or adjusted under 35 U.S.C. 154(b) by 0 days.

(21) Appl. No.: 09/580,468

(22) Filed: May 26, 2000

(51) Int. Cl.$^7$ .................................................. A61F 5/00
(52) U.S. Cl. .............................. 602/23; 602/16; 602/24
(58) Field of Search ....................... 602/5, 6, 16, 23–25, 602/60–62, 20; 128/882; 2/22, 311, 313; 623/39, 31–32

(56) References Cited

U.S. PATENT DOCUMENTS

| | | | |
|---|---|---|---|
| 1,445,437 A | * 2/1923 | Hoefftcke | |
| 2,055,066 A | * 9/1936 | Buchstein | 3/2 |
| 2,111,018 A | * 3/1938 | Ahler | 3/1 |
| 2,362,383 A | * 11/1944 | Lendinara | 287/1 |
| 2,545,843 A | 3/1951 | Cohan | |
| 2,654,365 A | * 10/1953 | Whitaker | 128/80 |
| 3,528,412 A | 9/1970 | McDavid | |
| 3,779,654 A | 12/1973 | Horne | |
| 3,902,482 A | 9/1975 | Taylor | |
| 4,088,130 A | 5/1978 | Applegate | |
| 4,243,027 A | * 1/1981 | LaCourse | 602/23 |
| 4,337,764 A | 7/1982 | Lerman | |
| 4,340,041 A | 7/1982 | Frank | |
| 4,481,941 A | 11/1984 | Rolfes | |
| 4,531,515 A | 7/1985 | Rolfes | |
| 4,574,790 A | * 3/1986 | Wellershaus | 602/23 |
| 4,579,558 A | * 4/1986 | Ramer | 623/31 |
| 4,865,024 A | 9/1989 | Hensley et al. | |
| 4,881,299 A | 11/1989 | Young et al. | |
| 4,881,532 A | 11/1989 | Borig et al. | |
| 4,928,676 A | 5/1990 | Pansiera | |
| 4,946,156 A | 8/1990 | Hart | |
| 4,982,732 A | 1/1991 | Morris | |
| 5,000,170 A | 3/1991 | Young et al. | |
| 5,038,765 A | 8/1991 | Young et al. | |
| 5,039,247 A | 8/1991 | Young et al. | |

(List continued on next page.)

FOREIGN PATENT DOCUMENTS

| | | | |
|---|---|---|---|
| DE | 000191678 A | * 11/1907 | .................. 602/5 |
| EP | 1068845 | 1/2001 | |
| EP | 1068846 | 1/2001 | |

OTHER PUBLICATIONS

"Team Management of Hip Revision Patients Using a Post–Op Hip Orthosis," by D. Lima et al. JPO/Journal of Prosthetics and Orthotics, vol. 6, No. 1. 1/Winter 1994.

(List continued on next page.)

Primary Examiner—Denise M. Pothier

(57) ABSTRACT

A hip orthosis includes a hip engaging unit that can be secured to the contours of a human hip. An appendant orthotic member is formed to extend diagonally about and to be fixed to a human appendage. A connector assembly, with a support plate with a curved configuration at an anchor location to permit adjustment, interconnects the hip engaging member and the appendant member and includes an articulated joint member to control flexion, extension, abduction and adduction. The joint members can include an adjustable linkage system extending across and connected to both sides of the articulated joint. A first link member can be adjusted in length to control the movement of the articulated joint. An adjustable hinge member having a rotational axis which is offset by approximately 90° from a rotational axis of the articulate joint can be set to limit a range of flexion, while movement of the articulated joint provides either a controlled abduction or adduction movement. Alternatively, the articulated joint can be formed by a roller and cam arrangement.

58 Claims, 7 Drawing Sheets

U.S. PATENT DOCUMENTS

| | | | |
|---|---|---|---|
| 5,052,379 A | | 10/1991 | Airy et al. |
| 5,054,476 A | | 10/1991 | Petrofsky et al. |
| 5,086,760 A | * | 2/1992 | Neumann et al. ............. 602/27 |
| 5,107,824 A | | 4/1992 | Rogers et al. |
| 5,188,584 A | | 2/1993 | Petrofsky et al. |
| 5,282,460 A | * | 2/1994 | Boldt |
| 5,286,251 A | * | 2/1994 | Thompson et al. ........... 602/23 |
| 5,344,391 A | | 9/1994 | Modglin |
| 5,361,418 A | | 11/1994 | Luzenske |
| 5,368,552 A | * | 11/1994 | Williamson ................... 602/23 |
| 5,385,536 A | * | 1/1995 | Burkhead et al. ............. 602/20 |
| 5,399,154 A | | 3/1995 | Kipnis et al. |
| 5,421,810 A | | 6/1995 | Davis et al. |
| 5,460,599 A | | 10/1995 | Davis et al. |
| 5,487,724 A | | 1/1996 | Schwenn |
| 5,538,499 A | | 7/1996 | Schwenn et al. |
| 5,620,412 A | | 4/1997 | Modglin |
| 5,630,791 A | | 5/1997 | Glynn |
| 5,647,378 A | * | 7/1997 | Farnum ...................... 128/876 |
| 5,662,595 A | * | 9/1997 | Chesher et al. ............... 602/20 |
| 5,681,267 A | | 10/1997 | Molino et al. |
| 5,681,270 A | | 10/1997 | Klearman et al. |
| 5,728,164 A | | 3/1998 | Ferrari et al. |
| 5,814,001 A | | 9/1998 | Schwenn et al. |
| 5,830,168 A | | 11/1998 | Finnell et al. |
| 5,860,943 A | | 1/1999 | Bloedau et al. |
| 5,938,629 A | | 8/1999 | Bloedau |
| 5,941,912 A | * | 8/1999 | Taylor .......................... 623/38 |
| 5,954,677 A | | 9/1999 | Albrecht et al. |
| 6,027,466 A | * | 2/2000 | Diefenbacher ............... 602/16 |
| 6,039,707 A | | 3/2000 | Crawford et al. |
| 6,090,057 A | * | 7/2000 | Collins ........................ 602/16 |
| 6,203,511 B1 | * | 3/2001 | Johnson et al. ................ 602/16 |
| 6,254,559 B1 | * | 7/2001 | Tyrrell .......................... 602/16 |
| 6,488,644 B1 | * | 12/2002 | Ostrom et al. ................ 602/16 |
| 6,494,853 B1 | * | 12/2002 | Rossi .......................... 602/16 |

OTHER PUBLICATIONS

"Helping Hips Hold Up," by D. Lima, BIOMECHANICS, Jun. 1998.

"Ultra–Guard Hip Orthosis" Brochure, Orthomedics, Rev. 9/93.

"The Post–Op System form Becker Orthopedic" Brochure, Becker Orthopedics, 1998.

"DHC . . . DOBI Hip Controller" Brochure, DOBI–Symplex 1995.

"NEWPORT®Hip System" Brochure, Orthomerica Products, Inc. 1995.

"Boston Post–Op Hip Orthosis" Brochure, Boston Brace International, Inc.

"Spinal Solutions "Sentry" Hip Orthosis", Spinal Solutions, Inc.

Bledsoe Brace Systems Catalog, 1995.

"The "ezy wrap 1267" Hinged Knee Brace" Brochure, 1995.

"Donjoy R.O.M. 4–Ponit Splint" Brochure, 1995.

"Donjoy Cool R.O.M. Splint", 1995.

"Donjoy Post–Op/Rehab Braces" Brochure, 1995.

"Matrix Medical Corporation CKM Brace # 89" Brochure, 1995.

Newport[3] Hip System Brochure, Orthomerica Products, Inc. (copy).

* cited by examiner

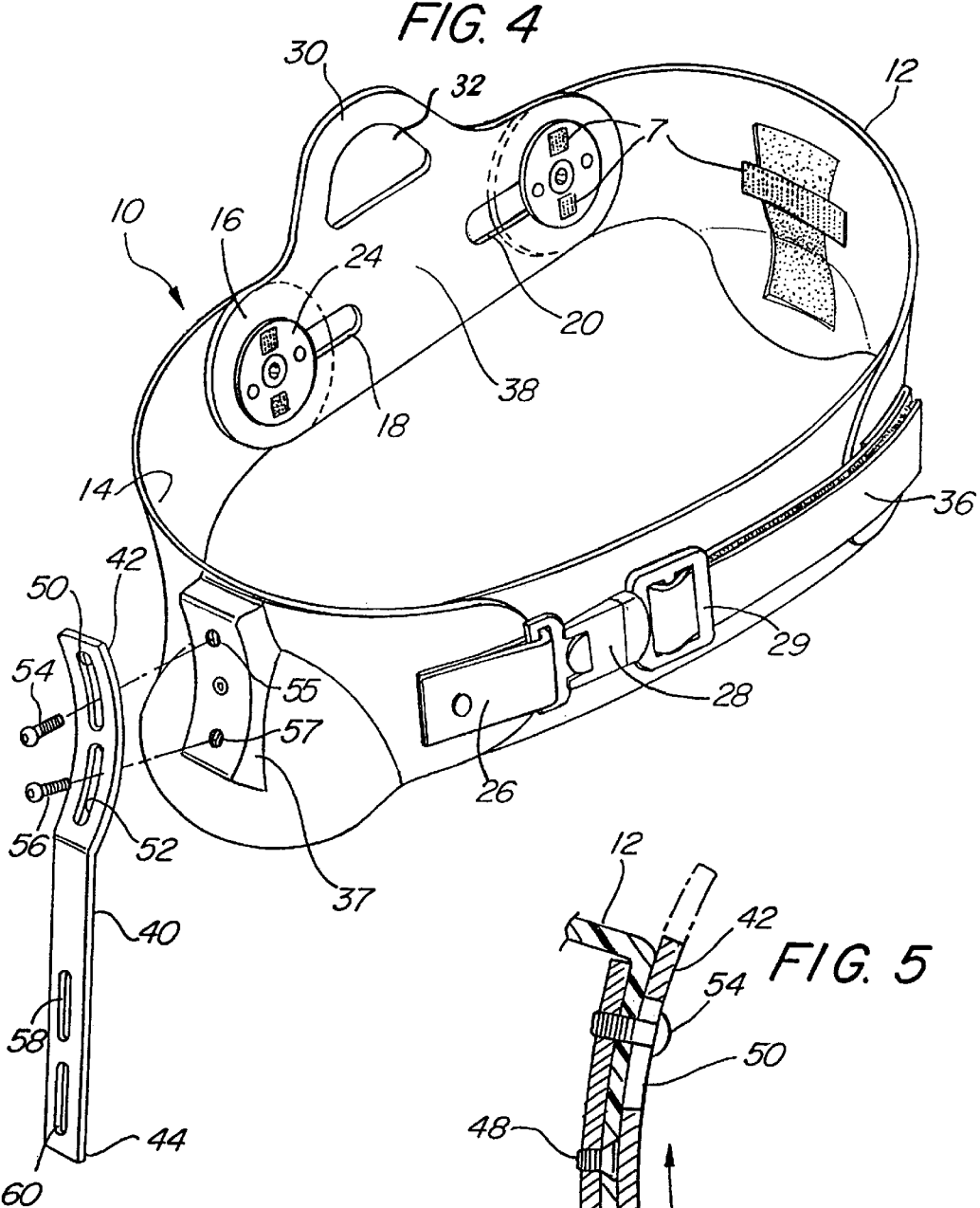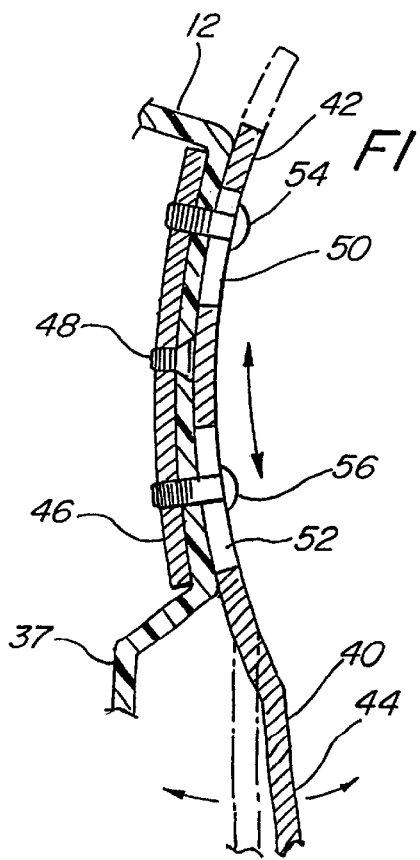

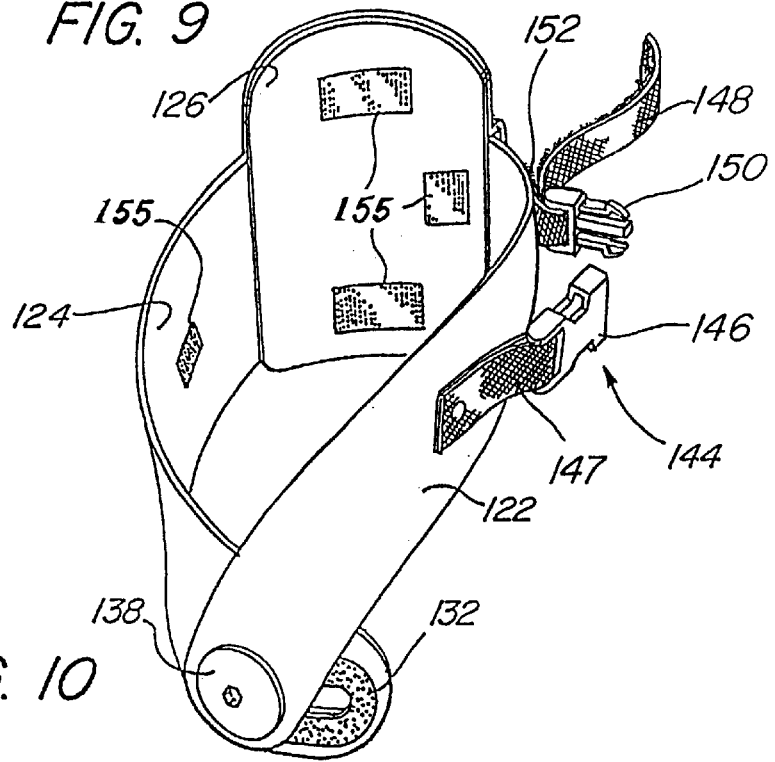
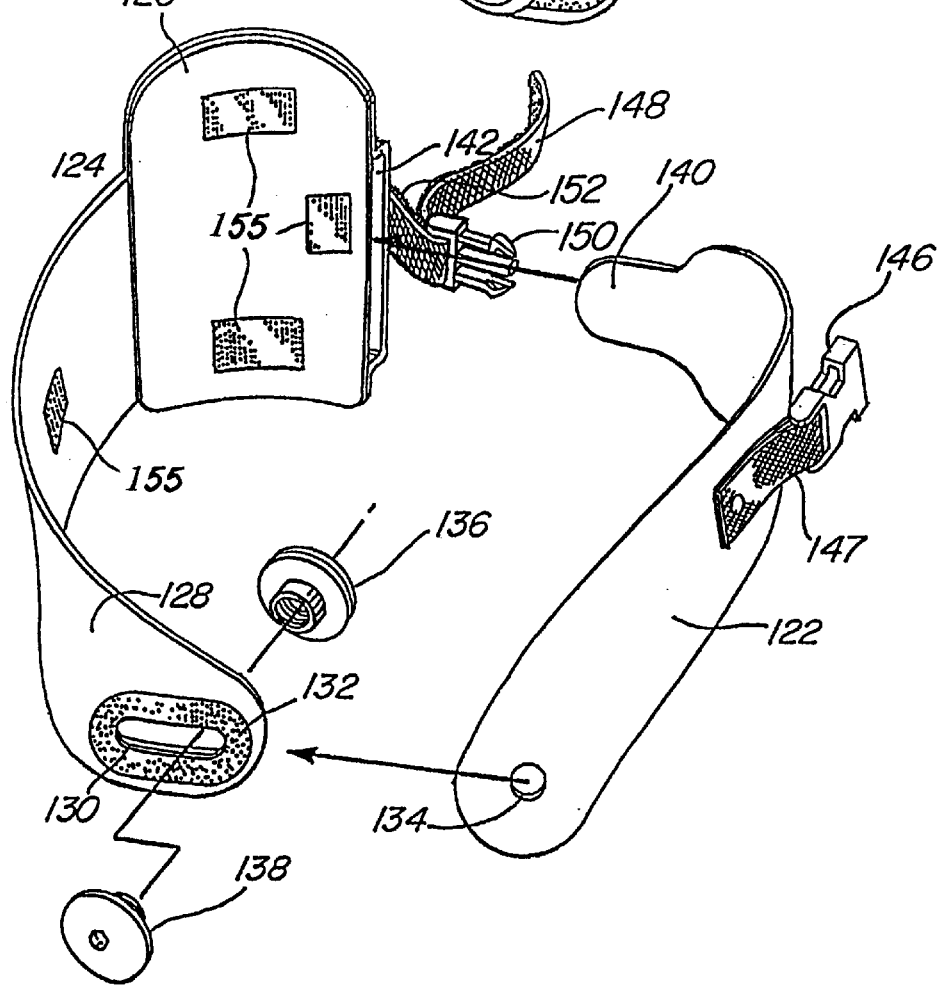

MODULAR ADJUSTABLE PROPHYLACTIC HIP ORTHOSIS AND ADDUCTION/ABDUCTION JOINT

BACKGROUND OF THE INVENTION

1. Field of the Invention

The present invention is directed to an orthotic brace and, more particularly, to an orthosis having modular component parts, such as a hip orthosis, that can address the postoperative treatment of a patient following hip arthoplatyies.

2. Description of Related Art

Orthotic management of hip joint compromise has been a challenge for orthopaedics, orthotists, and therapists when dealing with patients whose hip joints and their associated soft tissues, joint integrity, alignment, and bone and capsular components are compromised. A hip is a multidirectional joint capable of flexion, extension, internal and external rotation, adduction, and abduction. In addition to its mobility, the hip joint must absorb the force of fill weight-bearing and provide stability to the pelvis both for standing and for single support during gait. Additionally, during walking, while one hip is stabilized, the opposite leg must have the strength, range of motion, and structural integrity to advance.

The hip joint is a synovial ball and socket joint that consists of the articulation of the spherical head of the femur with the cup-like shape of the acetabulum. An acetabular labrum attaches to the bony rim of the acetabulum and cups around the head of the femur to hold it firmly in place. Various ligaments add strength to the articulation of the hip joint and a large number of muscles act on the hip joint. The gluteus medius is primarily associated with abduction. Anterior fibers assist with flexion and internal rotation. Posterior fibers assist with extension and external rotation. These muscle groups stabilize the pelvis during a single leg support.

Frequently, these muscle groups are compromised when surgical procedures are performed at the hip joint, especially during a hip replacement surgery. A significant problem that occurs when a hip joint has been compromised is dislocation of the hip joint. Thus, the femoral head can be driven out of the acetabulum. The hip is most susceptible to posterior dislocation when it is flexed past 90°, internally rotated and adducted. Examples of this action occur in every day living, such as sitting on a low chair and leaning forward while putting weight on the affected hip joint and internally rotating when coming to a standing position. Thus, common activities of daily living, specifically excessive hip flexion with loaded extremity and internal rotation on the affected side, can cause dislocation. Anterior dislocation also occurs when a hip is externally rotated, abducted, and flexed and if, for example, a knee is subject to a force, such as accidentally hitting an object. The neck of the femur or the greater trochanter levers the femur out of the acetabulum. To avoid these problems, an orthosis must be able to effectively control the limits of extension and rotation in a patient who has experienced an anterior dislocation.

The assignee of the present invention has provided orthoses to control extension and external rotation with a line of "NEWPORT®" hip system products.

See, for example, Team Management of Hip Revision Patients Using a Post-Op Hip Orthosis by Lima et al., Journal of Prosthetics and Orthotics, Vol. 6, No. 1, Winter/1994.

An example of an orthotic hip support can be found in U.S. Pat. No. 5,830,168, while a safety device to assist movement of a person can be found in U.S. Pat. No. 5,361,418. An orthopedic hip and leg abductor is disclosed in U.S. Pat. No. 5,361,418.

As the median age of the population becomes older, there are more occasions for the treatment of hip disorders and there is still a need to improve the function of such orthoses and their component parts in this medical field in an economical manner, while addressing a comfort level for the patient to encourage maximize prolonged usage.

SUMMARY OF THE INVENTION

The present invention is directed to a modular orthosis and to improvements in pre-fabricated component parts of the modular system for not only a hip orthosis, but for other broader applications in the orthotic field.

The orthosis can include a pelvic or hip engaging unit that is formed to conform to the contours of a human hip. This hip engaging unit can include multi-positional joints which can enable expansion, contraction, and rotation to permit a prefabrication of the hip engaging unit and a subsequent adjustment to the particular anatomy of the patient. The hip engaging unit can include first and second rigid outer hip engaging members with a relatively flexible rear connector plate adjustably interconnecting the first and second hip engaging members. A closure system can securely mount the hip engaging unit on the patient. The connector plate can have a bridge member extending vertically upward and across a hip band member to not only stiffen the connector plate from relative rotational movement, but also to provide a handle to permit an orthotist, a therapist or family care provider to assist in training the patient in the use of the orthosis.

An adjustable support plate assembly can be connected to an anchor location on the hip engaging unit. The support plate can have a securement portion adjacent the anchor location with a curved configuration to enable an adjustable movement of a distal end towards and away from the user. The distal end of the support plate can in turn be connected to an appendant orthotic member which can encircle and restrain movement of the leg of the patient.

Preferably, an adjustable hinge unit is provided to enable a range of both flexion and abduction movement. In one embodiment of the invention, an adjustable linkage system can extend across an articulated joint to permit a setting of a range of abduction that can vary with flexion. Flexion can be controlled with a variable setting hinge member. A link member that can be adjusted in length is pivotally affixed on either side of the articulated joint. The link member can be fixed at a location offset from a first rotational axis of the hinge member. The articulated joint has a second rotational axis which can be offset approximately 90° from the first rotational axis of the hinge members whereby movement about the first rotational axis will cause movement of the articulated joint about the second rotational axis. Since the hinge member is adjustable to control the range of flexion and extension and the link member is adjustable to control adduction and abduction, a controlled compound motion is afforded the patient.

An alternative adjustable hinge unit can utilize a variable setting hinge member with a pivotal joint member connecting the hinge member to a bar that is attached to the appendant orthotic member. A follower roller and cam member can control the bar's movement in adduction and abduction as the hinge member permits the hip joint to flex and extend.

The appendant orthotic member can be pre-fabricated in the form of a sleeve member or diagonal semi-rigid cylindrical band that can be adjusted in dimension to fit the thigh and knee portion of the patient. The sleeve member is formed of a relatively rigid plastic with a degree of flex and adjustable joints are provided for varying an encircling dimension of the sleeve member on the appendage to provide a custom fit for the user. Since the outer upper side of the sleeve member is longitudinally displaced from an opposite lower portion adjacent the knee, corresponding fixation points are provided to prevent rotational displacement of the sleeve member about the leg. Appropriate resilient pads can be removably fastened to both the hip engaging unit and the appendant sleeve member to directly bear against the patient's body.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 4 is a perspective view of the hip engaging member;

FIG. 5 is a cross-sectional view of an anchor location on the first hip engaging member;

FIG. 9 is a perspective view of an appendant orthosis for attachment to a leg of a patient;

FIG. 10 is a partial exploded view of the appendant orthosis of FIG. 9;

DETAILED DESCRIPTION OF THE PREFERRED EMBODIMENTS

The following description is provided to enable any person skilled in the orthotic art to make and use the invention and sets forth the best modes contemplated by the inventors of carrying out their invention. Various modifications, however, will remain readily apparent to those skilled in the art, since the general principles of the present invention have been defined herein specifically to provide an improved modular component orthosis which can be combined together to form an adjustable prophylactic hip orthosis and adduction/abduction joint.

The modular components of the present invention can be combined together to provide an orthosis that can be pre-fabricated and subsequently adjusted to meet the specific needs and sizes of various patients. Thus, the cost of customized orthoses can be avoided while retaining the advantages of a customized fitting to meet the specific needs of the patient. The utilization of the various modular components can be advantageously incorporated in different types of orthotic applications, since individually they each represent improvements in design and function. Collectively, the modular components can advantageously provide an improved orthosis.

A particular example of such an orthosis is an adjustable prophylactic hip orthosis and abduction joint. While the present invention is described in this environment, it should be readily appreciated that the metes and bounds of this invention are not so limited, since one or more of the modular components can be advantageously utilized in other orthotic applications. For example, the hip engaging unit of the present invention can be utilized to provide a stable platform for supporting orthoses treating shoulder and arm appendages. Likewise, it can provide a stable platform for other orthoses, such as an orthopaedic leg abductor for resisting muscular contraction of the type disclosed in U.S. Pat. No. 5,814,001 and incorporated herein. Another example of an orthosis that can utilize component parts of the present invention, such as the hip engaging unit, the adjustable support plate, and the connector plate, can be seen in orthopaedic shoulder braces having adjustable pelvic and arm supports shown, for example, in U.S. Pat. No. 5,538,499 and U.S. Pat. No. 5,487,724 which are incorporated herein by reference.

Figure 1:
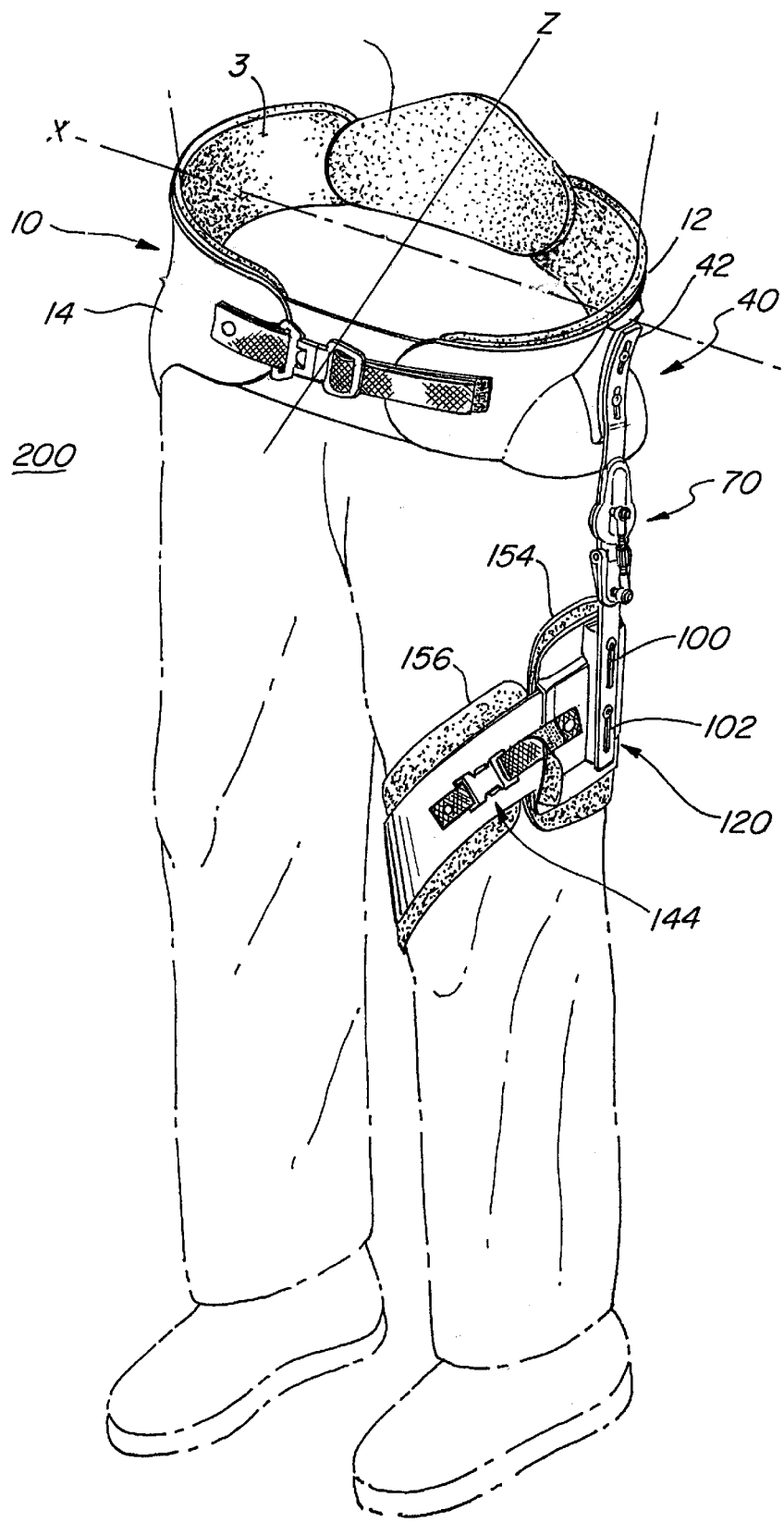
FIG. 1 is a front perspective view of the modular component parts formed in a hip orthosis of the present invention.

Referring to FIG. 1, an embodiment of the present invention is disclosed as an adjustable hip orthosis 200. The adjustable hip orthosis is created from pre-fabricated modular component parts that can be custom-adjusted to match the particular size of the patient and the prescribed range of motions permitted for that patient, including flexion, extension, adduction, and abduction.

The hip orthosis 200 includes a pelvic or hip engaging unit 10, as shown in FIG. 4, having a first hip engaging member 12 and a second hip engaging member 14. Each of the hip engaging members 12 and 14 include a relatively rigid plastic shell of a shape to capture and conform to a side of a patient's hip and leg. The plastic can be a high or low density polyethylene, a polypropylene or co-polymers thereof, which can be heat-molded into a shape which conforms to the contours of the average human hip. Removable resilient pads 3 such as neoprene, polyurethane foam or polyethylene foam or other medically acceptable resilient pads are mounted within each hip engaging member to provide comfort to the user.

A flexible plastic connector plate 16 has a pair of elongated slots 18 and 20. An abrasive, gritted, knurled or cross-hatched surface 34 can extend peripherally around the respective elongated slots 18 and 20. An abrasive tape or patch can be adhered about the slots 18 and 20 to provide the textured surfaces. By providing such a friction textured surface, both on the connector plate 16 and on a matching surface of the respective first hip engaging member 12 and the second hip engaging member 14, both horizontal and relatively rotational adjustments can be made for a customized fit on the patient and then a subsequent compressive tightening by the fasteners 22 and 24, which extends through the respective slots 18 and 20, can lock these respective joints into place without the need for incremental settings. A tool, such as an Allen wrench (not shown), may be utilized to tighten the fasteners. As can be appreciated, neoprene pads can be attached, for example, by a hook and nap material 7, such as Velcrog® to the interior of the hip engaging unit 10.

A strap 26 can be anchored on the first hip engaging member 12 and can have an adjustable buckle 28 attached to the strap 26. Another strap 36 is anchored on the second hip engaging member 14 with a buckle engaging member 29 at the other end. Additionally, a hook and nap fastener unit with the nap material being provided on the strap 36 and the hook material being provided adjacent the anchor point to the first hip engaging member 12 permits the hip engaging unit 10 to be adjusted and removably fastened to the user.

The connector plate 16 adjustably interconnects the first and second hip engaging members 12 and 14 and further includes a bridge member 30 extending vertically upward and across a lower band member 38 of the connector plate 16. Thus, the connector plate 16 has the lower band member 38 with the elongated slots 18 and 20 and the vertical upper extending bridge portion 30 to thereby stiffen the connector plate 16 against movement traverse to a plane X, Z centrally aligned with a circumference of the hip engaging unit 10, see FIG. 1. The connector plate 16 is formed from a flexible plastic material, such as low-density polyethylene or polypropylene and permits a greater degree of flex of the connector plate 16 in a direction lying across the plane centrally aligned with the circumference of the hip engaging unit 10. Such an arrangement helps stabilize and prevent relative rotation of the first and second hip engaging members 12 and 14. The aperture 32 further creates a convenient handle that permits a care provider to firmly grasp the rear of the hip engaging unit 10 to provide support for the patient as he/she is acclimatizing himself/herself to the use of this orthosis. An anchor location 37 can be formed on either of the hip engaging members as will subsequently be described. Further details of features of the hip engaging unit 10 can be found in U.S. Pat. No. 5,830,168, which is incorporated herein by reference.

Referring to FIG. 1 and FIG. 5, the hip engaging unit 10 is disclosed with an anchor location 37 on the first hip engaging member 12 for adjustably securing a support plate 40 having a curved securement portion 42 and a straight distal portion 44. As shown in FIG. 4, the anchor location 37 is located on the hip engaging member 14. The anchor location will be adjacent the patient's hip socket that was replaced. The first hip engaging member 12 includes a metal anchor plate 46, such as aluminum, which is secured on an interior skin of the rigid plastic shell of the first hip engaging member 12. A fastener 48 can lock the anchor plate 46 to the rigid hip engaging shell. A pair of elongated slots 50 and 52 or fastening structure on the securement portion 42 can receive respective fasteners or bolts 54 and 56. These fastener bolts or members can be screwed into threaded bores 55 and 57 in the anchor plate 46 and when loosened permit the curved securement portion 42 to radially slide in a vertical plane relative to the hip engaging member 12 and the anchor plate 46 to thereby permit an adjustment of the position of the distal portion 44 relative to the leg appendage of the user. Thus, the dotted lines in FIG. 5 disclose such an adjustment. This adjustment prevents impingement of the orthosis on the hip of the patient and provides a custom fit for full figure patients.

As can be appreciated, the straight distal portion 44 can also have elongated slot apertures 58 and 60 to permit a relative connection to a hinge member to be subsequently described. The support plate 40 can be made from a relatively heavy gauge aluminum or other material to provide adequate strength.

Since the support plate 40 can be appropriately adjusted by sliding its position relative to its anchored position on the hip engaging unit 10, the distal position can be appropriately positioned for linking with an appended orthotic member which can be attachable to a user appendage. In the embodiment disclosed herein, the user appendage is a leg, but as can be readily appreciated, with an appropriate reversing of position, the support plate 40 could also extend vertically upward to permit a linking with an appended orthotic member for supporting an arm, shoulder, etc. The fastening structure of the elongated slots 50 and 52 with the fastener bolts 54 and 56 enables an adjustable movement relative to the anchor location 37 to permit sliding movements of the distal end 44 towards and away from a user. When the fastener bolts 54 and 56 are appropriately fastened to the anchor plate 46 that can have threaded bore holes for receiving the fastener bolts 54 and 56, the plastic shell of the hip engaging member is captured in a sandwich fashion to provide additional strength and to distribute the appropriate load over a wider area of the hip engaging unit 10.

Figure 2:
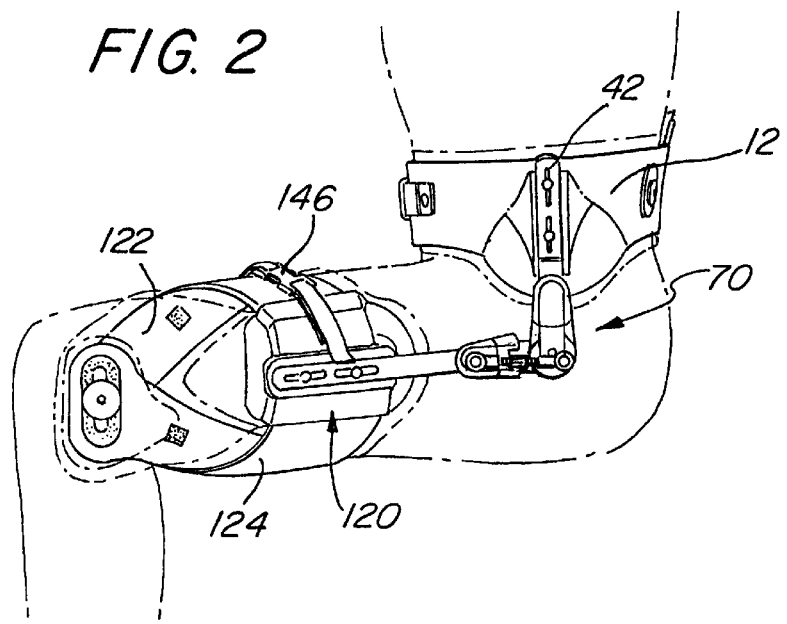
FIG. 2 is a side perspective view of the hip orthosis in a setting position.
Figure 3:
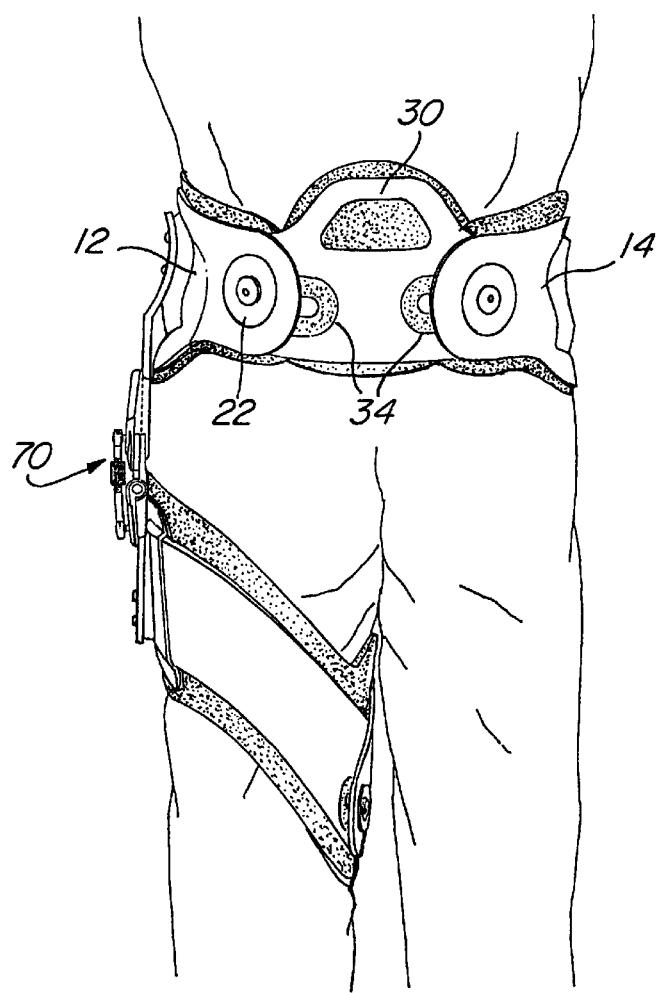
FIG. 3 is a rear elevated view of the hip orthosis.
Figure 6:
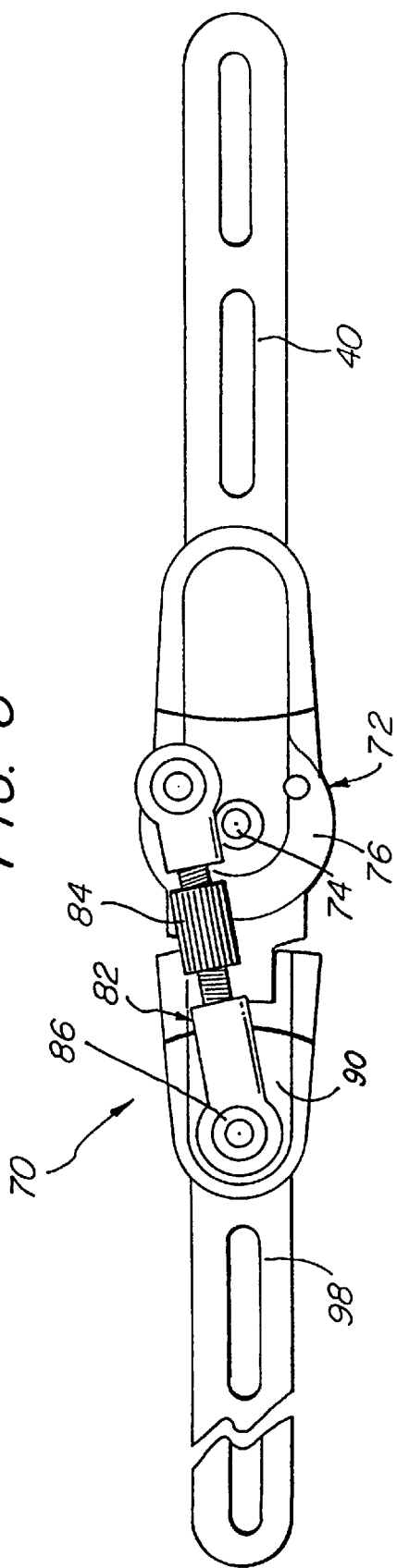
FIG. 6 is a plan view of an adjustable hinge unit.

As can be seen from FIGS. 1–3 and FIGS. 6–8, an adjustable hinge unit 70 can be connected to the distal portion 44 of the support plate 40. The adjustable hinge unit 70 provides a controlled three-dimensional range of movement to permit a range of flexion and also abduction and adduction. Various forms of orthopaedic hinge assemblies have been utilized to provide an adjustable range of movement about an axis. An example of an orthopaedic hinge assembly for use with this leg brace can be found in U.S. Pat. No. 5,460,599, which is incorporated herein by reference. Another example can be found in U.S. Pat. No. 5,421,810, which is also incorporated herein by reference. The adjustable hinge unit 70 of the present invention employs a hinge member 72 having a relatively compact profile and an adjustable range of movement to control flexion and extension of the appendage about a first rotational axis 74. As shown in FIGS. 1–3, the adjustable hinge unit is disclosed in a hip orthosis. While the hinge member 72 is preferably of the type disclosed in U.S. Pat. No. 5,460,599, other hinge members can be utilized to control the amount of flexion and extension in the present invention.

Figure 8:
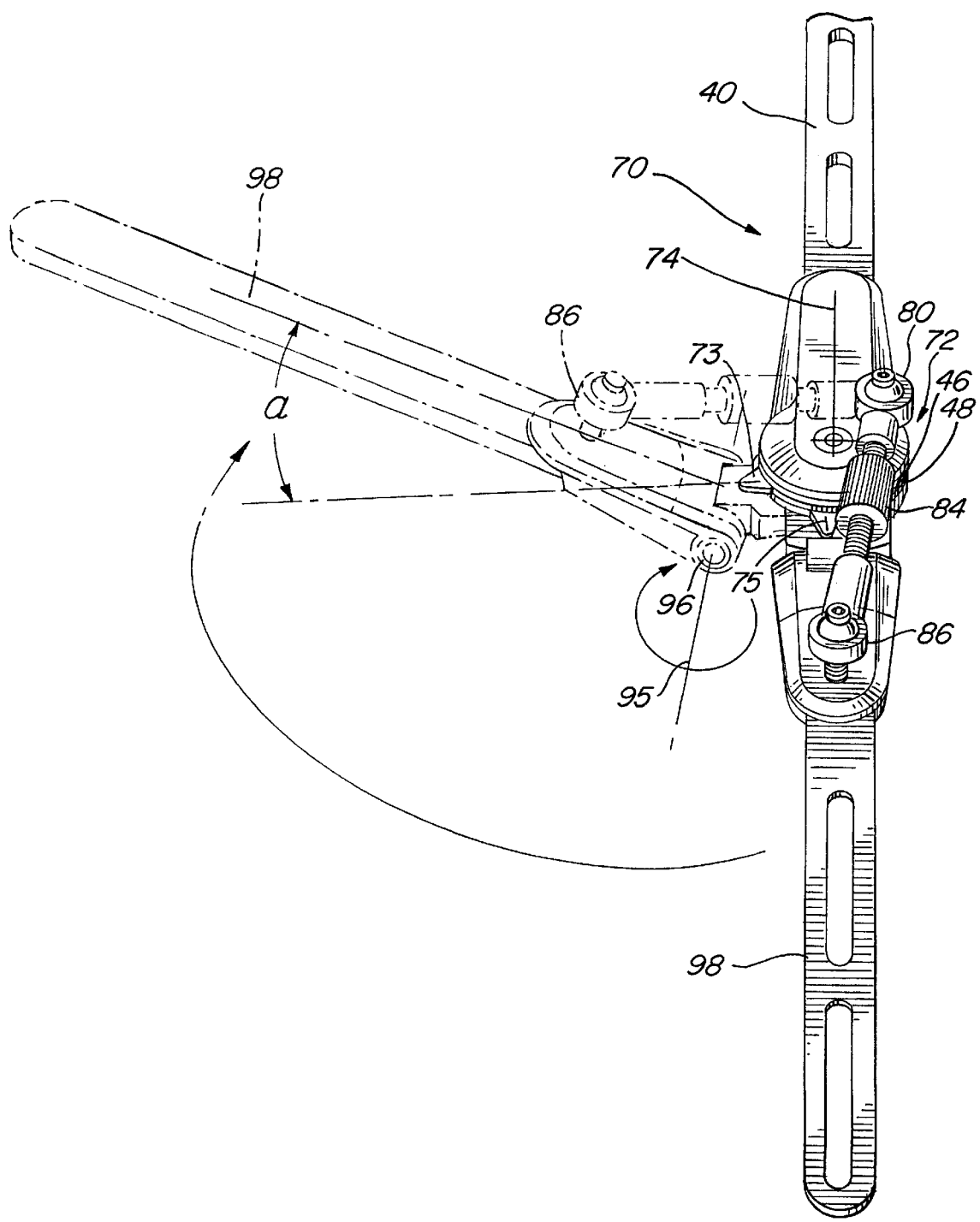
FIG. 8 is a perspective view of the adjustable hinge unit.

The hinge member 72 includes a housing structure 76 that can support the rotational movement of a pair of flat disc adjuster members 46 and 48, see FIG. 8. These adjuster members 46 and 48 have peripherally complementary indentations or gear teeth that can be adjustably fastened together or locked by a fastener member (not shown) that can adjustably extend inward or outward in a radial direction from the first rotational axis 74 of the hinge member 72. Accordingly, adjustment of indicator tabs 73 and 75 can adjust the range of flexion movement by moving arcuate openings (not shown) in the adjuster members that receive a stop member (not shown) to define the limited range of movement.

The housing member 76 can further support a support post 78. The support post 78 is radially offset from the first rotational axis 74 and can provide, approximately at its distal end, a universal joint 80. The universal joint 80 is connected to a lever arm 82. In the embodiment of the invention shown in FIGS. 6–8, the lever arm 82 can include a turn buckle 84 that enables the length of the lever arm 82 to be adjusted along its longitudinal axis so that it can be shortened or lengthened. The lever arm 82 has at its other end a second universal joint 86 which is mounted on the distal end of a support post 88. The support post 88 extends upward from a second housing member 90. Depending on whether the adjustable hinge unit 70 is to serve a left or right leg of the patient, the location of the support post 78 can be changed. On either side, the support post 78 is radially offset from the first rotational axis 74 so that the effective distal end of the lever arm 82 is displaced and causes relative movement of the support post 88. Thus, an adjustable linkage system extends across and connects on opposing sides of the articulated joint member 70 as shown in FIG. 7.

The first housing member 76 can be adjustably mounted to the distal end of the support plate 40. Elongated slots 58 and 60 can receive fastener bolts 92 and 94, respectively, for securement of the hinge member 72 to the support plate 40. Interconnecting the first housing member 76 and the second housing member 90 is an articulated or pivotal joint member 96 with a second axis of rotation 95 that is offset by approximately 90° to the first axis of rotation 74 of the hinge member 72. While 90° is the preferred offset angle, the present invention can utilize other angles, since the purpose of the adjustable hinge unit 70 is to control both flexion and extension about one axis, while controlling adduction and abduction about a second axis in a relative compound motion.

Figure 7:
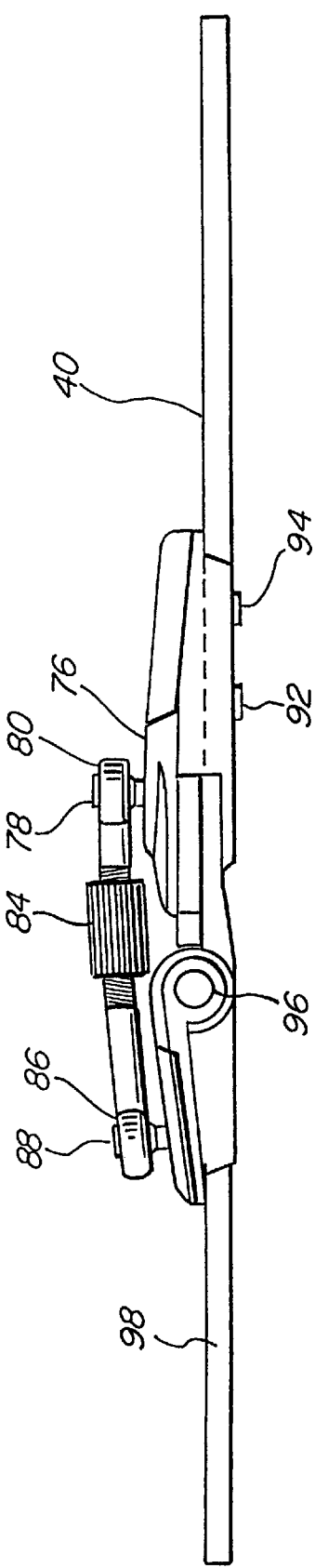
FIG. 7 is a side view of the adjustable hinge unit.

As shown in FIG. 7, the length of the lever arm 82 permits the plate or bar 98 to be relatively co-planar with a support plate 40 when there is 0 degrees of flexion. This could be equivalent, for example, to the alignment shown in FIG. 1 and FIG. 3. As the degree of flexion increases, such as shown in FIGS. 2 and 8, the bar 98 with an appendant orthotic member attached to the thigh and knee area of the user will rotate about the first rotational axis 74 of the hinge member 72. Since the point of attachment of the lever arm 82 is offset from the rotational axis 74, there will be a displacement of the lever arm 82. Since the lever arm 82 has been adjusted by the turnbuckle 84 and the length of the lever arm 82 is fixed after the adjustment, there will be a rotation about the second rotational axis 95 of the pivotal joint member 96 causing either abduction or adduction, depending upon the particular setting of the length of the lever arm 82. Since a hip can be particular susceptible to posterior dislocation when it is flexed past 90 degrees, internally rotated and abducted, the amount of abduction can be controlled along with the range of flexion. Thus, the respective support posts 78 and 88 can provide a fixed distance along with the adjustable lever arm 82. The first housing member 76 and the second housing member 90 which are connected to the pivotal joint member 96 are the other components of the linkage assembly that can control the adduction and abduction of the orthotic brace.

Thus, the adjustable linkage extension system extending across and connected on both sides of the pivotal joint member 96 includes the lever arm 82 that can be adjusted in length to provide a force applying unit to control the adduction and abduction movement of the pivotal joint member 96. As can be appreciated, the lever arm 82 can be adjusted in other ways than a turnbuckle 84. The turnbuckle 84 provides minute adjustments but a series of apertures or holes could be provided in a lever arm or a series of replaceable link arms to provide fixed increments of adjustment. Additionally, if desired, the universal joints 80 and 86 could be spring-biased to float on the respective support posts. The particular configuration of the lever arm 82 can be further varied in order to accommodate the profile and size of the pivotal joint member 96. For example, there could be bowed configuration to the lever arm 82 to maintain a low profile. A removable cap or cover can be attached to the lever arm 82 to deflect contact. As shown in FIG. 8, support bar 98 is rotated rearward in abduction by as much as 45° about the second axis of the pivotal joint 96, as shown by arrow "a" as the flexion is rotated 90° about the first rotational axis 74 of the hinge member 72. This compound motion can be appropriately adjusted by the care provider by adjusting and setting the index tabs 73 and 75 and by turning the turnbuckle 84 to precisely set the permissible range of flexion and abduction required by the specific patient.

Figure 11:
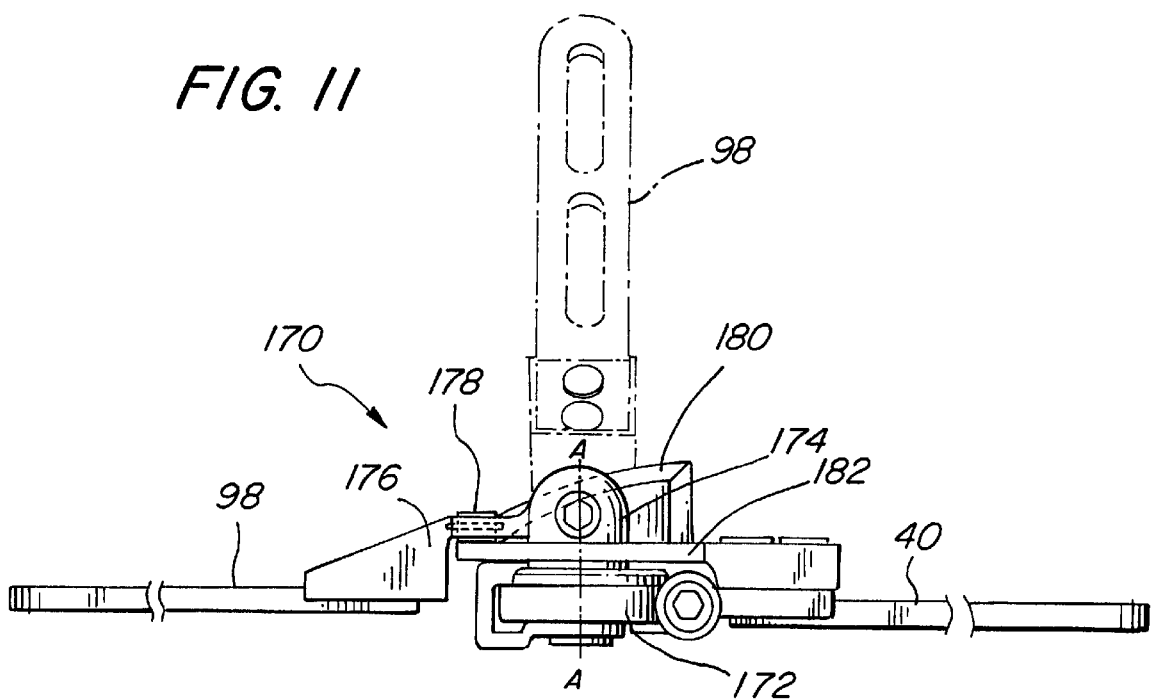
FIG. 11 is a side view of an alternative embodiment of an adjustable hinge unit.
Figure 12:
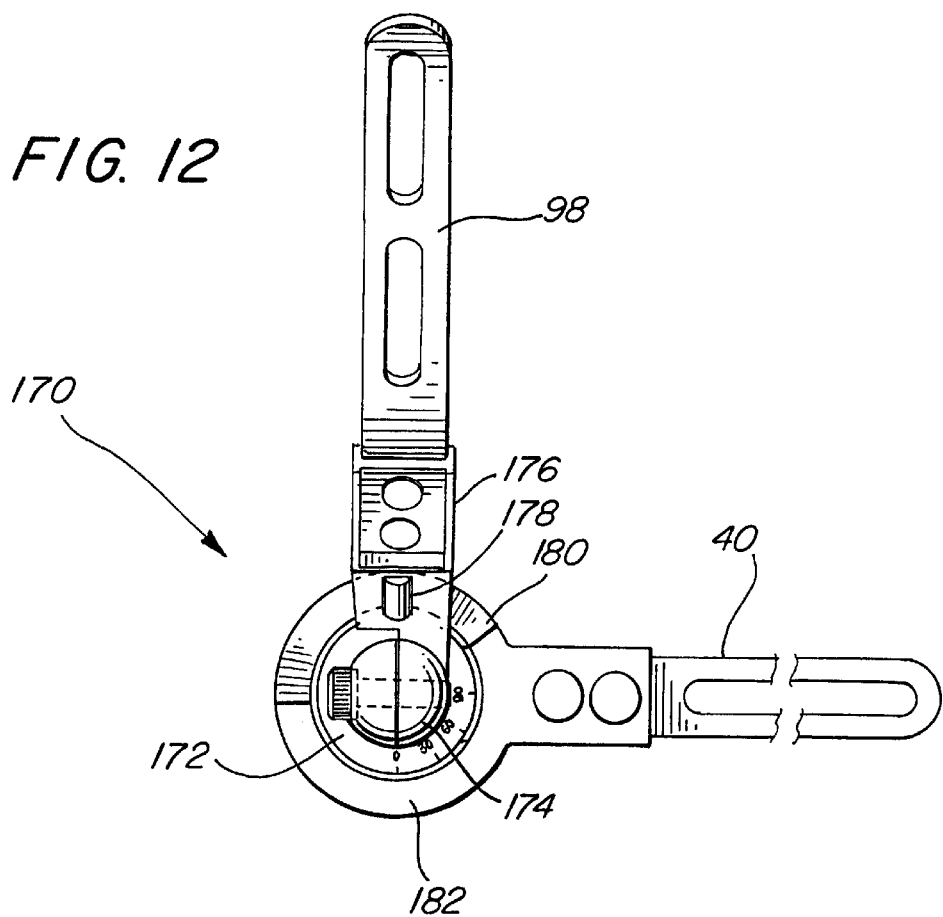
FIG. 12 is a plan view of the alternative embodiment.

An alternative adjustable hinge assembly 170 is shown in FIGS. 11 and 12. The hinge assembly 170 includes an adjustable hinge member or unit 172 that can support a rotational movement to control flexion and extension about a central axis A—A. The extent of rotational movement can be set in a conventional manner. The hinge member 172 is relatively compact in profile and is connected to the support plate 40.

Aligned with the axis A—A, a pivotal joint member 174 is mounted above the hinge member 172 and is connected by an arm member 176 to the bar 98. The arm member 176 rotatably mounts a follower member such as a roller 178 that rotates about a shaft journaled on the arm member 176. A cam member 180 having a sloping cam surface engages the roller 178 to provide a force applying unit which defines a range of abduction and adduction as the hip joint flexes and extends. The cam member 180, as shown, has a fixed predetermined cam surface. However, the supporting ring 182 could be rotatable to permit an adjustment with the cam surface appropriately designed. Alternatively, a set of modular combinations (not shown) of different ring and cam profiles can be provided and mounted for a particular patient range of abduction and adduction.

As shown in FIG. 11 by the phantom lines of bar 98, the combination of roller 178 and cam member 180 rotates the bar 98, about the pivotal joint member 174, traverse to the plane of rotation of the hinge member 172.

As further shown in FIG. 1, the support bar 98 also includes a pair of elongated slots 100 and 102. Fastener bolts 104 and 106 can be adjustably mounted within the elongated slots 100 and 102 to attach an appendant orthotic member 120, such as a leg restrainer in the environment of the hip orthosis 200. The attachment of the hip engaging unit 10 and the appendant orthotic member 120 provide two anchor points on the user's body relative to the patient's hip joint, while the support plate 40, adjustable hinge unit 70, and support bar 98 cooperatively define an adjustable positional connector relationship between the hip engaging unit 10 and the appendant orthotic member 120.

As can be appreciated, if there is an uncontrolled relative rotation of the hip engaging unit 10 or of the appendant orthotic member 120, the desired control for flexion and abduction or adduction may be compromised. The hip conforming configuration of the first and second hip engaging members 12 and 14 assist in locking the hip engaging unit 10 about the pelvic region of the user. A leg restrainer that basically encircles only a thigh portion of the user's leg will primarily be engaging soft tissue and may permit a relative rotation about the thigh. The additional amount of contractive force that can be inserted against the patient's thigh is limited by the comfort of the patient so that conventional restrainers that grasp only the thigh portion may permit some undesirable rotation. The appendant orthotic member 120 of the present invention has been heat formed to extend diagonally about and to be fixed to a human appendage, such as the leg, with a contact on the outer thigh and an inner contact adjacent the inside of the knee portion of the user. As can be appreciated, the knee portion in most users provides a greater immediacy of contact, since the skeletal structure of the knee joint has less fat or soft tissue.

Thus, by having one side of the appendant orthotic member 120 longitudinal displaced along the leg appendage of the user from an opposite side of the appendant orthotic member, it will provided correspondingly longitudinally displaced fixation points to prevent rotational displacement. The appendant orthotic member 120 is bifurcated into a first section 122 and a second section 124. The second section 124 is connected to an injection molded Nylon® slotted anchor plate or housing 126. The first section 122 and second section 124 are formed from a relatively rigid plastic of an acrylic modified PVC, such as Kydex® sold by Kleerdex, Inc.

The first section 122 and second section 124 have relatively elongated band configurations that collectively form a diagonal cylindrical configuration when attached together. The distal ends of the first and second sections relative to the anchor plate 126 are adjustably connected together to permit sizing to the particular dimension of the leg appendage. The distal end of the second section 124 is enlarged to a somewhat oval configuration 128 having a central elongated slot 130 with an appropriately textured friction perimeter band 132 of the same type as described on the hip engaging unit 10. The distal end of the first section 122 has an aperture 134 that can receive a plastic male fastener 136 that can be secured to a female fastener 138. The matching surface of the distal end of the first section 122 extending around the aperture 134 can have a complementary friction textured perimeter (not shown) to provide a secure compression friction fit with the textured perimeter band 132. The proximal end of the first section 122 is formed into an insertion tongue member 140 for mounting within a slot 142 in the anchor plate 126. A buckle and strap closure unit 144 retains the tongue member 140 within the slot, opening 142 of the anchor, housing 126. The buckle member 146 is anchored to the anchor housing 126. A male member 150 on the strap 148 can removably lock to the buckle member 146 on strap 147 and the strap 148 portion can have an appropriate nap portion that will affix to a hook strip 152, such as a Velcro® fastener arrangement.

Likewise, individual hook patches 155 can be adhered to the inner surface, for example, of the anchor plate housing 126 and also to the inner surfaces of the first section 122 and second section 124 whereby neoprene pads 154 and 156 can be held in place to provide cushioning when the first section 122 is hooked into the anchor housing 126 and forms with the second section 124 the appendant orthotic member 120 that will extend diagonally about the human leg. Extra padding can be provided over distal ends that bear against the knee. Since the elongated bands of relatively rigid plastic that form the first section 122 and second section 124 extend diagonally, they provide a firm anchoring on the inside of the knee and the outside of the thigh to prohibit relative rotation. However, there is sufficient flex in the appendant orthotic structure 120 to permit the user to remove the connection to the leg when the male member 150 is released from the buckle member 146. The adjustment to the size of the leg is made by the distal end joint adjustment, and the buckle member 146 only holds the tongue 140 in a fixed position.

An additional advantage of the particular design of the appendant orthotic 120 is hat the diagonal configuration permits the patient to be more comfortable when seated, s shown in FIGS. 2 and 3, since it is displaced from the seat and crotch area of the user. Thus, the patient is not necessarily directly sitting on the second section 124. If the adjustable hip orthosis 200 is worn under clothing, for example, by a patient with a dress or gown, the ability to use a toilet seat is provided without removing the orthosis, while still maintaining a sanitary condition. Since a patient will experience greater comfort while his range of motion and movement will be precisely controlled, the patient will be encouraged to wear the orthosis during the prescribed time period to prevent dislocation of a hip. As can be appreciated, the post-operative treatment of a patient can frequently extend from six weeks to six months, and patients who do not wear their orthoses will be more susceptible to problems.

The preferred embodiment disclosed herein incorporates the contributory benefits of each of the modular components to provide a precisely controllable orthotic solution to the post-operative treatment of a patient with hip arthroplasties. As can be appreciated, however, the individual component parts can also be utilized in other configurations of orthoses to realize the economical advantages of a pre-fabricated orthosis for a patient.

In the appended claims, the invention will be described in accordance with the sixth paragraph of 35 U.S.C. § 112 only when the claim terminology of "means" is expressly incorporated into the body of the claims.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An orthosis comprising:
    a hip engaging unit formed to conform to the contours of a human hip;
    an appendant member formed to extend about and to be fixed to a human appendage; and
    a connector assembly interconnecting the hip engaging unit and the appendant member including an articulated joint member with an adjustable extension-flexion movement and an adjustable abduction-adduction movement that is controlled by the amount of movement of the extension-flexion movement, wherein the connector assembly includes an adjustable linkage system extending across and connected on both sides of the articulated joint member, including a first link member that can be adjusted in length to control the movement of the articulated joint member and an adjustable hinge with a first rotational axis, which is offset by approximately 90° from a second rotational axis of the articulated joint member, the adjustable hinge can be set to limit a range of flexion, while movement of the articulated joint member provides either adduction or abduction.

2. The orthosis of claim 1, further including a second and third link member connected respectively to the first link member and respectively to either side of the articulated joint member.

3. The orthosis of claim 1, wherein the first link member includes a turn buckle, which is adjustable to vary the length of the first link member.

4. The orthosis of claim 1, wherein a first support post is connected adjacent one side of the articulated joint member and a second support post is connected adjacent the other side of the articulated joint member and the first link member is pivotally connected between the first and second support posts.

5. The orthosis of claim 4, wherein the first link member includes a turn buckle which is adjustable to vary the length of the first link member.

6. The orthosis of claim 1, wherein the connector assembly includes a support plate having a securement portion adjacent an anchor location on the hip engaging unit and a distal portion for linking with the appendant member which is attachable to the user appendage, the securement portion having a curved configuration and a fastening structure that enables an adjustable movement relative to the anchor location to permit sliding movements of the distal portion towards and away from the user; and a fastener member for securing the curved configuration to the anchor location to maintain a desired position for the distal portion relative to the user.

7. The orthosis of claim 6, wherein the anchor location has a complementarily curved location to the curved configuration of the securement portion.

8. The orthosis of claim 7, wherein the distal portion has a straight portion.

9. The orthosis of claim 8, wherein the securement portion has an elongated slot as the fastening structure for receiving the fastener member.

10. The orthosis of claim 6, wherein the hip engaging unit includes first second hip engaging members formed to encircle and conform to the contours of a human and a connector plate adjustably interconnecting the first and second hip engaging members, connector plate including a bridge member extending vertically upward and across relative to connections with the respective first and second hip engaging members to stiffen the connector plate from movement traverse to a plane centrally aligned with a circumference of the hip engaging unit while permitting a greater degree of flex of the connector plate in directions lying across the plane.

11. The orthosis of claim 10, wherein the connector plate includes a band member with respective apertures for receiving fasteners to affix the connector plate to the respective hip engaging members.

12. The orthosis of claim 11, wherein the bridge member is sufficiently spaced from the band member to provide a handle for grasping by a human hand.

13. The orthosis of claim 12, wherein the first and second hip engaging members are respectively formed with rigid plastic outer shells configured to conform to the sides of the human hip.

14. The orthosis of claim 13, wherein the connector plate extends across a rear of the human hip and is formed of a flexible plastic material.

15. The orthosis of claim 10, wherein the appendant member is bifurcated into a first section and a second section which are adjustable connected together to permit mounting on the user.

16. The orthosis of claim 15, wherein the appendant member is a relatively rigid plastic band of a diagonal cylindrical configuration.

17. The orthosis of claim 16, wherein the appendant member is affixed by one section of the first and second sections to an anchor plate.

18. The orthosis of claim 17, wherein the anchor plate has a slot for removably securing the other section of the first and second sections.

19. The orthosis of claim 18, wherein distal ends of the first and second sections relative to the anchor plate are adjustably connected together.

20. The orthosis of claim 19, wherein one of the distal ends is larger than the other distal end and includes an elongated slot and a fastener member for securing the distal ends together by fastening within the slot.

21. The orthosis of claim 19, wherein a frictional surface is provided on each distal end to enhance a gripping securement when the fastener member exerts a compression force to the distal ends.

22. The orthosis of claim 19, further including a female connector secured to the anchor plate and an adjustable strap with a male connector secured to the other of the first or second section.

23. The orthosis of claim 19, further including a flexible pad member connected to the appendant member for interfacing with the user appendage.

24. The orthosis of claim 1, wherein the appendant member is sized and configured to extend diagonally about the human appendage, one side of the appendant member is longitudinally displaced from an opposite side of the appendant member to provide corresponding longitudinally displaced fixation points to prevent rotational displacement when mounted about the appendage.

25. An orthosis comprising:
a hip engaging member formed to conform to the contours of a human hip including an anchor member with a curved concave surface fixed to the hip engaging member;
an appendant member formed to extend about and be fixed to. a human appendage;
a support plate having a securement portion adjacent the anchor member on the hip engaging member and a distal portion for linking with the appendant member which is attachable to the user appendage, the securement portion having a curved convex configuration complimentary to the curved concave surface of the anchor member that enables an adjustable movement relative to the anchor member to permit sliding movement on the distal portion laterally and outwardly away from the user, and a fastening structure along the curved convex configuration; and
a fastener member for fixedly securing the curved configuration of the securement portion to the anchor member by operatively contacting the fastening structure to maintain the desired position of the distal portion relative to the user.

26. The orthosis of claim 25, wherein the distal portion has a straight portion.

27. The orthosis of claim 25, wherein the securement portion has an elongated slot as a fastening structure for receiving the fastener member.

28. An orthosis comprising:
a hip engaging unit formed to conform to the contours of a human hip;
an appendant member formed to extend about and to be fixed to a human appendage; and
a connector assembly interconnecting the hip engaging unit and the appendant member including an articulated joint member with a first adjustable hinge member having a first rotational axis to provide an adjustable extension-flexion movement and a second hinge member having a second rotational axis orientated approximately 90° from the first rotational axis and offset radially from the first rotational axis to provide an adjustable abduction-adduction movement and a force applying unit responsive to the movement of the extension-flexion movement to provide abduction-adduction movement, wherein, the connector assembly includes an adjustable linkage system extending across and connected on opposing sides of the articulated joint member, including a first link member that can be adjusted in length to control the movement of the articulated joint member.

29. The orthosis of claim 28 further including a second and third link member connected respectively to the first link member and respectively to either side of the articulated joint member.

30. The orthosis of claim 28, wherein the first link member includes a turn buckle, which is adjustable to vary the length of the first link member.

31. The orthosis of claim 28, wherein a first support post is connected adjacent one side of the articulated joint member and a second support post is connected adjacent the other side of the articulated joint member and the first link member is pivotally connected between the first and second support posts.

32. The orthosis of claim 31, wherein the first link member includes a turn buckle which is adjustable to vary the length of the first link member.

33. The orthosis of claim 28, wherein the connector assembly includes a support plate having a securement portion adjacent an anchor location on the hip engaging unit and a distal portion for linking with the appendant member which is attachable to the user appendage, the securement portion having a curbed configuration and a fastening structure that enables an adjustable movement relative to the anchor location to permit sliding movements of the distal portion towards and away from the user; and a fastener member for securing the curved configuration to the anchor location to maintain a desired position for the distal portion relative to the user.

34. The orthosis of claim 33, wherein the anchor location has a complementarily curved location to the curved configuration of the securement portion.

35. The orthosis of claim 34, wherein the support plate has a straight distal portion.

36. The orthosis of claim 35, wherein the securement portion has an elongated slot as the fastening structure for receiving the fastener member.

37. The orthosis of claim 34, wherein the hip engaging unit includes first and second hip engaging members formed to encircle and conform to the contours of a human hip and a connector plate adjustably interconnecting the first and second hip engaging members, the connector plate including a bridge member extending vertically upward and across relative to connections with the respective first and second hip engaging members to stiffen the connector plate from movement traverse to a plane centrally aligned with a circumference of the hip engaging unit, while permitting a greater degree of flex of the connector plate in directions lying across the plane.

38. The orthosis of claim 37, wherein the connector plate includes a band member with respective apertures for receiving fasteners to affix the connector plate to the respective hip engaging members.

39. The orthosis of claim 38, wherein the bridge member is sufficiently spaced from the band member to provide a handle for grasping by a human hand.

40. The orthosis of claim 39, wherein the first and second hip engaging members are respectively formed with rigid plastic outer shells configured to conform to the sides of the human hip.

41. The orthosis of claim 39, wherein the connector plate extends across a rear of the human hip and is formed of a flexible plastic material.

42. The orthosis of claim 37, wherein the appendant member is bifurcated into a first section and a second section which are adjustable connected together to permit mounting on the user.

43. The orthosis of claim 42, wherein the appendant member is a relatively rigid plastic band of a diagonal cylindrical configuration.

44. The orthosis of claim 43, wherein the appendant member is affixed by one section of the first and second sections to an anchor plate.

45. The orthosis of claim 44, wherein the anchor plate has a slot for removably securing the other section of the first and second sections.

46. The orthosis of claim 45, wherein distal ends of the first and second sections relative to the anchor plate are adjustably connected together.

47. The orthosis of claim 46, wherein one of the distal ends is larger than the other distal end and includes an elongated slot and a fastener member for securing the distal ends together by fastening within the slot.

48. The orthosis of claim 46, wherein a frictional surface is provided on each distal end to enhance a gripping securement when the fastener member exerts a compression force to the distal ends.

49. The orthosis of claim 46, further including a female connector secured to the anchor plate and an adjustable strap with a male connector secured to the other of the first or second section.

50. The orthosis of claim 46, further including a flexible pad member connected to the appendant member for interfacing with the user appendage.

51. An orthosis comprising:
a hip engaging unit formed to conform to the contours of a human hip;
an appendant member formed to extend about and to be fixed to a human appendage; and
a connector assembly interconnecting the hip engaging unit and the appendant member including an articulated joint member with an adjustable extension-flexion movement and an adjustable abduction-adduction movement that is controlled by the amount of movement of the extension-flexion movement, wherein the connector assembly includes an adjustable linkage system extending across and connected on both sides of the articulated joint member, including a first link member that can be adjusted in length to control the movement of the articulated joint member, and an adjustable hinge adjacent the articulated joint member, the adjustable hinge has a first rotational axis offset by approximately 90° from a second rotational axis of the articulated joint member, the first link member is movably affixed adjacent the adjustable hinge and radially offset from the first rotational axis, whereby movement of the adjustable hinge about the first rotational axis will cause movement of the articulated joint member about the second rotational axis, and adjustment of the adjustable linkage system provides adduction and abduction movements about the second rotational axis.

52. The orthosis of claim 51, wherein a first support post is connected adjacent one side of the articulated joint member and a second support post is connected adjacent the other side of the articulated joint member and the first link member is pivotally connected between the first and second support posts.

53. The orthosis of claim 52, wherein the first link member includes a turn buckle which is adjustable to vary the length of the first link member.

54. An orthosis comprising:
a hip engaging unit formed to conform the contours of a human hip;
an appendant member formed to extend about and to be fixed to a human appendage; and
a connector assembly interconnecting the hip engaging unit and the appendant member including an articulated joint member with an adjustable extension-flexion movement and an adjustable abduction-adduction movement that is controlled by the amount of movement of the extension-flexion movement, wherein the connector assembly includes an adjustable linkage system extending across and connected on both sides of the articulated joint member, including a first link member that can be adjusted in length to control the movement of the articulated joint member, and a support plate having a securement portion adjacent an anchor location on the hip engaging unit and a distal portion for linking with the appendant member which is attachable to the user appendage, the securement portion having a curved configuration and a fastening structure that enables an adjustable movement relative to the anchor location to permit sliding movements of the distal portion towards and away from the user; and a fastener member for securing the curved configuration to the anchor location to maintain a desired position for the distal portion relative to the user, wherein the hip engaging unit includes first and second hip engaging members formed to encircle and conform to the contours of a human hip and a connector plate adjustable interconnecting the first and second hip engaging members, the connector plate including a band member with respective apertures for receiving fasteners to affix the connector plate to the respective hip engaging members and a bridge member extending vertically upward and across relative to connections with the respective first and second hip engaging members to stiffen the connector plate from movement traverse to a plane centrally aligned with a circumference of the hip engaging unit while permitting a greater degree of flex of the connector plate in directions lying across the plane, wherein the bridge member is sufficiently spaced from the band member to provide a handle for grasping by a human hand.

55. An orthosis comprising:

a hip engaging unit formed to conform to the contours of a human hip;

an appendant member formed to extend about and to be fixed to a human appendage; and a connector assembly interconnecting the hip engaging unit and the appendant member including an articulated joint member with an adjustable extension-flexion movement and an adjustable abduction-adduction movement that is controlled by the amount of movement of the extension-flexion movement, wherein the connector assembly includes an adjustable linkage system extending across and connected on both sides of the articulated joint member, including a first link member with a turn buckle that can be adjusted in length to control the movement of the articulated joint member.

56. An orthosis comprising:

a hip engaging unit formed to conform to the contours of a human hip;

an appendant member formed to extend about and be fixed to a human leg; and an adjustable joint member for interconnecting the hip engaging unit and the appendant member to permit a controlled extension and flexion and a controlled abduction and adduction of the leg including a first hinge member that provides an adjustable range of extension and flexion and a second hinge member connected on a first side to the first hinge member that provides abduction and adduction movement approximately traverse to a plane containing the extension and flexion movement and a lever arm anchored at one end to the adjustable joint member for movement with the first hinge member and at the other end on a second side of the second hinge member whereby the extension and flexion movement of the first hinge member exerts a force on the appendant member through the lever arm to the second side of the second hinge member to provide a corresponding controlled abduction and adduction movement.

57. The orthosis of claim 56 further including a first support post pivotally connected to the lever arm that moves with the hinge member and a second support post pivotally connected to the lever arm on the second side of the articulated joint member.

58. The orthosis of claim 56 further including a turn buckle which is adjustable to vary the length of the lever arm.

* * * * *